United States Patent
Gyory et al.

[11] Patent Number: 6,163,720
[45] Date of Patent: Dec. 19, 2000

[54] LAYERED RATE CONTROLLING MEMBRANES FOR USE IN AN ELECTROTRANSPORT DEVICE

[75] Inventors: J. Richard Gyory, North Oaks, Minn.; Ronald P. Haak, Palo Alto, Calif.

[73] Assignee: Alza Corporation, Mountain View, Calif.

[21] Appl. No.: 09/204,820

[22] Filed: Dec. 3, 1998

Related U.S. Application Data

[60] Provisional application No. 60/068,047, Dec. 18, 1997.

[51] Int. Cl.[7] .................................................. A61N 1/30
[52] U.S. Cl. ............................................................ 604/20
[58] Field of Search ................ 604/19, 20; 424/447–449

[56] References Cited

U.S. PATENT DOCUMENTS

| | | |
|---|---|---|
| 3,797,494 | 3/1974 | Zaffaroni . |
| 4,156,067 | 5/1979 | Gould ........................................ 528/73 |
| 4,250,878 | 2/1981 | Jacobsen et al. . |
| 4,391,278 | 7/1983 | Cahalan et al. . |
| 4,416,274 | 11/1983 | Jacobsen et al. ........................ 604/20 |
| 4,419,092 | 12/1983 | Jacobsen et al. ........................ 604/20 |
| 4,474,570 | 10/1984 | Ariura et al. ............................. 604/20 |
| 4,526,176 | 7/1985 | Bremer et al. . |
| 4,537,680 | 8/1985 | Barth ...................................... 210/316 |
| 4,557,723 | 12/1985 | Sibalis .................................... 604/20 |
| 4,639,244 | 1/1987 | Rizk et al. ............................... 604/19 |
| 4,640,689 | 2/1987 | Sibalis .................................... 604/20 |
| 4,702,732 | 10/1987 | Powers et al. .......................... 604/20 |
| 4,722,726 | 2/1988 | Sanderson et al. ...................... 604/20 |
| 4,731,049 | 3/1988 | Parsi ...................................... 604/20 |
| 4,786,277 | 11/1988 | Powers et al. .......................... 604/20 |
| 4,793,825 | 12/1988 | Benjamin et al. ..................... 604/891.1 |
| 4,817,594 | 4/1989 | Juhasz . |
| 4,878,892 | 11/1989 | Sibalis et al. ............................ 604/20 |
| 4,883,457 | 11/1989 | Sibalis .................................... 604/20 |
| 4,886,514 | 12/1989 | Maget ................................... 604/891.1 |
| 4,904,475 | 2/1990 | Gale et al. ............................. 424/449 |
| 4,919,648 | 4/1990 | Sibalis .................................... 604/20 |
| 4,927,408 | 5/1990 | Haak et al. .............................. 604/20 |
| 4,931,046 | 6/1990 | Newman ................................ 604/20 |
| 4,935,345 | 6/1990 | Guilbeau et al. ........................ 435/14 |
| 4,942,883 | 7/1990 | Newman . |
| 4,959,208 | 9/1990 | Chakrabarti et al. .................... 424/78 |
| 5,080,646 | 1/1992 | Theeuwes et al. ...................... 604/20 |
| 5,232,438 | 8/1993 | Theeuwes et al. ...................... 604/20 |
| 5,423,739 | 6/1995 | Phipps et al. ........................... 604/20 |
| 5,573,668 | 11/1996 | Grosh et al. ........................... 210/490 |
| 5,681,568 | 10/1997 | Goldin et al. ........................ 424/184.1 |
| 5,894,021 | 4/1999 | Okabe et al. .......................... 424/449 |
| 5,900,250 | 5/1999 | Lee et al. .............................. 424/448 |

FOREIGN PATENT DOCUMENTS

| | | |
|---|---|---|
| 0 273 167 | 11/1987 | European Pat. Off. . |
| 0 748 636 A2 | 12/1996 | European Pat. Off. ......... A61N 1/30 |
| 0263179 | 10/1989 | Japan . |
| 0648232 | 2/1979 | U.S.S.R. . |
| 2 184 016 | 6/1987 | United Kingdom . |
| WO 97/12644 | 4/1997 | WIPO ........................... A61N 1/30 |

OTHER PUBLICATIONS

CRC Handbook of Chemistry and Physics, 67th ED., pp. D–151–D–158 (1987).
Encyclopedia of Polymer Science and Engineering, vol. 9, pp. 97–139 (1987).

*Primary Examiner*—Sharon Kennedy
*Assistant Examiner*—Michael J Hayes
*Attorney, Agent, or Firm*—Owen J. Bates; D. Byron Miller; Steven F. Stone

[57] ABSTRACT

The disclosed invention relates to an improved electrotransport device. The improvement relates to a membrane assembly including a low porosity membrane adhered or sealed to one or two high porosity membranes. The high porosity membranes protect the low porosity membrane from being damaged by components or contaminates on the body surface and/or in the drug reservoir which can lead to undesirable passive flux and/or insufficient iontophoretic flux. As a result, the electrotransport device having the membrane assembly more reliably, precisely, and accurately delivers drug and/or therapeutic agent through the body surface by electrotransport.

16 Claims, 2 Drawing Sheets

LAYERED RATE CONTROLLING MEMBRANES FOR USE IN AN ELECTROTRANSPORT DEVICE

RELATED APPLICATIONS

This application claims the benefit of the U.S. Provisional Application Ser. No. 60/068,047, filed Dec. 18, 1997.

FIELD OF INVENTION

This invention relates to electrotransport devices to deliver drugs and therapeutic agents to a patient. The invention also relates to rate controlling membranes for use in electrotransport devices.

BACKGROUND OF THE INVENTION

Electrotransport devices and transdermal patches are drug delivery systems that are capable of satisfying many needs facing the health care industry. For example, attempts have been made to control and increase the rate of delivery, reduce drug and agent degradation, and reduce the risk of infection. However, such goals have become more difficult to reach as the molecular size of the drugs and therapeutic agents to be delivered increases. Such drugs and agents include peptides, polypeptides and proteins.

An electrotransport device generally includes at least two electrodes and a source of electrical power. Each electrode is in electrical communication and physical contact with some portion of the skin, nails, mucus membrane or other membrane surface of the body. One electrode is generally referred to as the active or donor electrode, and the other electrode is referred to as the counter or return electrode. The donor electrode also includes a donor reservoir which contains the drug or therapeutic agent to be delivered, and the counter electrode includes a counter reservoir that generally contains an electrolyte. In combination, the electrodes close the electrical circuit through the patients body surface.

The drug or therapeutic agent is a charged molecule, or ion, that is carried through the body surface by applied current. The charge of the drug or agent determines whether the donor electrode is the cathode or anode. For example, the donor electrode is the anode when the drug is positively charged, and the counter electrode is the cathode. Alternatively, the donor electrode is the cathode when the drug is negatively charged, and the counter electrode is the anode.

The reservoirs are generally in the form of a pouch, a cavity, a porous sponge or pad, or a pre-formed gel or polymer composite body. The donor reservoir is in electrical communication with the respective electrode. Semipermeable membranes typically have a limited number of minute pores to control the rate of drug delivery.

Known electrotransport devices may also include a semipermeable membrane that controls the rate of drug delivery. The membrane is located between the donor reservoir and the body surface. The membrane is also in electrical and ion-transmitting communication with the donor reservoir and the body surface. Membranes are also used in the counter reservoir to control passive delivery of a drug or therapeutic agent.

However, there may be a need for a semipermeable membrane that more accurately and precisely controls passive drug/agent flux. Prior membranes were disadvantaged in that membranes having small pore size (about 0.09 micron diameter) and low porosity (about $4 \times 10^5$ pathways per $cm^2$ or 0.003% by volume) prevented passive flux, but failed to allow therapeutically sufficient current after lamination and assembly. Prior devices are also disadvantaged in that the membrane can be damaged or compromised by oils and other contaminants from the skin or drug reservoir during operation of the device. The contamination may cause occlusions in the membrane that affect the rate of drug delivery. For example, if the membrane loses resistance, the drug may passively flux into the body surface at significant levels. Membranes may also have excessive resistance that hampers drug delivery reducing efficacy and depleting the electrical power source. Such losses of control over the rate of drug delivery are acutely disadvantageous where the drug is an analgesic, such as an opioid.

Membrane pores may also be deleteriously affected when the membrane is contacted with the body surface. Body oils, dirt particulates and other contaminates on the skin are transferred to the semipermeable membrane clogging pores in the membrane. Hydrophobic components in the donor and/or counter reservoirs may also clog membrane pores or cause occlusions. Such damage to the semipermeable membrane compromises control, precision and accuracy of the drug delivery rate.

Prior devices are further disadvantageous because the membrane pores may be altered when the membrane is affixed to the donor and/or counter reservoir. Semipermeable membranes are affixed using adhesives and/or laminates under heat and/or pressure that can cause occlusions in and deformation of the membrane pores. Such damage deleteriously affects the passive and/or iontophoretic flux of the drug/agent.

SUMMARY OF THE INVENTION

The present invention is advantageous over such prior devices because, among other reasons, a semipermeable membrane assembly is employed. The present membrane assembly, which is for use only in an electrotransport device, is substantially unaffected by skin oils and other contaminants or by hydrophobic components in the reservoir. The present invention also includes a method of attaching the membrane to the reservoir without the problems associated with affixing it with adhesives and laminates under heat and pressure.

Another advantage of the present invention is that, as shown in the preferred embodiments, the low porosity membrane is structurally supported by the one or more, preferably two, high porosity protective layers. In addition, the present membrane assembly achieves steady state drug delivery faster than comparable conventional electrotransport systems. For example, the present membrane assembly will generally be less flux resistant than a comparable single low porosity layer having similar thickness and structural integrity. As a result, the present invention increases structural integrity without substantially affecting the time needed to achieve steady state drug delivery/flux.

Another aspect of the invention is a method of reducing occlusive effects in a rate-controlling membrane caused by body oils, adhesives, particulate contaminates and/or hydrophobic components. Such occlusions may deleteriously affect or compromise the passive flux of such membranes in an electrotransport device.

Still another aspect of the invention is an electrotransport device including a rate-controlling membrane assembly positioned between the donor reservoir and the body surface. The assembly includes a low porosity layer adjacent the reservoir and a high porosity layer positioned between the low porosity layer and the body surface. In another aspect of the invention, the high posority layer is adjacent the donor reservoir, and the low porosity layer is positioned between the high porosity layer and the body surface.

Yet another aspect of the invention is an electrotransport device including a second high porosity protective layer whereby the low porosity layer is sandwiched between the high porosity layers. The high porosity membrane(s) may be affixed to the device and/or low porosity membrane by lamination without substantially altering the porosity of the low porosity, rate-controlling layer. As such, a significant amount of pore occlusion may be tolerated when the membrane assembly is affixed to the donor reservoir. As a result, the precision and accuracy of the low porosity layer is not significantly compromised. The high porosity layer protects the low porosity layer from exposure to body oils and particulate contaminates causing occlusions and other damage.

Preferably, the high porosity membranes of the present invention have a porosity sufficient to permit a drug delivery rate substantially greater than the therapeutic drug delivery rate. More preferably, the porosity is greater than or equal to about 10%, and even more preferably, greater than or equal to about 20%.

Preferably, the low porosity, rate-controlling membranes of the present invention have a porosity sufficiently low to permit a drug delivery rate substantially equal to a therapeutic drug delivery rate. More preferably, the porosity is less than or equal to about 1%, and even more preferably, less than or equal to about 0.1%.

Yet another aspect of the invention is a method of making a low and high porosity membrane for use in assembling the membrane assembly. For example, the membrane may be made by lithographically depositing a film on a preformed low porosity substrate. Preferably, the low or high porosity membranes are photolithographically formed on either major opposing surface of an appropriate pre-formed substrate, low or high porosity. The high porosity membranes may be affixed to the low porosity membrane by using adhesives or by applying pressure and/or heat seals. Preferably, substantially only the periphery of the high porosity membrane is adhesively affixed or laminated. Preferably, the low porosity membrane is sandwiched between the high porosity layers protecting the low porosity layer from damage.

BRIEF DESCRIPTION OF THE DRAWINGS

The invention is described in further detail hereinbelow with reference to preferred embodiments and the accompanying drawings wherein.

DETAILED DESCRIPTION OF THE INVENTION

One preferred embodiment of the invention relates to a rate-controlling membrane assembly for use in an electrotransport device. The membrane assembly is designed and assembled in an electrotransport device to improve the accuracy and precision of the drug and/or therapeutic agent flux. The accuracy and precision of the flux is improved by having the assembly include high and low porosity layers. In one embodiment, a high porosity layer is positioned between the donor reservoir and the low porosity layer which is adjacent to the body surface.

The high porosity layer has a porosity sufficiently high before assembly or operation that, upon acquiring pore occlusions, the high porosity layer is more porous than the low porosity layer. Such occlusions may be caused during assembly by adhesives or laminates, or exposure to contaminates during assembly or operation. As a result, the drug/agent delivery rate is substantially unaffected by damage to the high porosity membrane during assembly or operation of the electrotransport device.

In another preferred embodiment of the invention, a rate-controlling membrane assembly includes a high porosity membrane positioned between the low porosity layer and the body surface. The high porosity layer has a porosity sufficiently high before assembly or operation that, upon acquiring pore occlusions or damage during assembly or operation of the device, the high porosity layer is more porous than the low porosity layer. The high porosity layer protects the low porosity layer from being compromised. For example, the high porosity layer may be damaged by oils or particulate contaminates on the body surface. Occlusions may form and/or pores may be clogged or otherwise obstructed. Such damage may also occur when the membrane are affixed and assembled.

In another preferred embodiment of the invention, a rate-controlling membrane assembly includes a first high porosity membrane positioned between a low porosity membrane and the body surface and a second high porosity membrane positioned between the low porosity membrane and the donor reservoir. As a result, the low porosity membrane is protected from ingredients and contaminants in the drug/agent reservoir and from oils and particulate contaminants on the body surface. The low porosity membrane is also protected from adhesives and laminates during assembly.

Preferably, the rate-controlling membrane assembly employs two high porosity membranes protecting a low porosity membrane. The assembly more accurately and reliably delivers drugs and/or therapeutic agents at a more precise flux. As in the other embodiments, the high porosity layers have a porosity sufficiently high before assembly or operation that, upon acquiring pore occlusions or damage during assembly or operation of the device, each high porosity layer is more porous than the low porosity layer.

Figure 1:
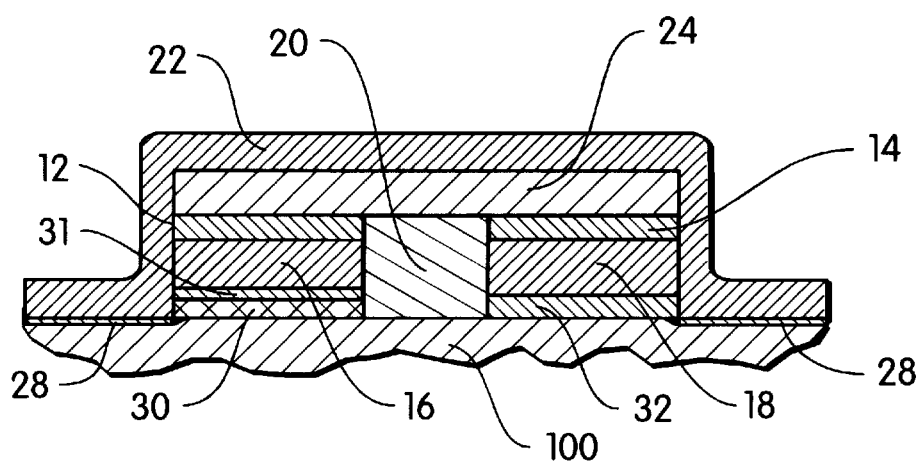
FIG. 1 is a schematic sectional view of an exemplary electrotransport device having an exemplary membrane assembly.

In a preferred embodiment of the invention, as shown in FIG. 1, an electrotransport device 10 includes a donor electrode 12 and a counter electrode 14. The donor and counter electrodes 12,14 are positioned adjacent to the donor and counter reservoirs 16,18 respectively. The donor reservoir 16 contains the drug or agent to be delivered, and the counter reservoir 18 contains a biocompatible electrolytic salt. Alternatively, drug and/or therapeutic agent may be delivered from the donor and counter electrodes simultaneously or in an alternating manner. In that case, a rate-controlling membrane assembly is employed in conjunction with the counter electrode and reservoir.

An insulator 20 separates the donor electrode 12 and donor reservoir 16 from the counter electrode 14 and counter reservoir (which is optional). The insulator 20 prevents direct ion or electron transport between the donor electrode 12 or reservoir 16 and the counter electrode 14 or reservoir 18. The insulator 20 prevents the device 10 from short-circuiting. The insulator 20 may be made from a material sufficiently impermeable to water and ions to ensure agent ion transport through the body surface 100,200,300. Preferably, the insulator 20 is made from polyisobutylenes or ethylene vinyl acetate or a material capable of forming sufficiently strong bonds with the polymeric reservoirs to achieve structural integrity.

As shown in FIG. 1, the electrotransport device 10 also includes a backing layer 22 constructed from an electrically insulating or non-conducting material. A power source 24 supplies electrical power to the electrodes 12,14. The power source 24 comprises a battery, which can include without limitation, thin film and lithium batteries; and a controller for regulating the flow of electricity. The controller comprises various electronic circuits for regulating the flow of electricity, such electronic components including without limitation a microprocessor. The backing layer 22 is preferably made from a material having negligible electrical conductivity insulating the device 10. The backing layer 22 prevents short-circuits due to external moisture and structurally supports the adjacent components of the device 10.

The electrodes 12,14 are constructed of an electrically conductive material such as a metal. Preferably, the electrodes 12,14 are made from foil or screen, or they are made using a chemical process, such as deposition, painting/coating, calendaring, film evaporation, or by embedding metal powder in a binder matrix. Exemplary metals include silver, zinc, silver chloride, aluminum, platinum, stainless steel, gold and titanium. The most preferred embodiment includes an anodic electrode made of silver and a cathodic electrode made of silver chloride.

The electrodes 12,14 may also be constructed from a conductive filler dispersed in a polymer matrix. For example, the conductive filler is preferably powdered graphite, carbon fibers, or other fillers known in the electrode art. The polymer matrix is preferably a hydrophobic polymer known in the electrode art to minimize any interaction or reaction with any water that may be present in the respective reservoir. The counter and donor electrodes 12,14 may be constructed from dissimilar metals or have different half cell reactions. The electrodes 12,14 may also generate at least a portion of the required electrical power. An exemplary galvanic couple is the silver silver chloride electrode assembly where the standard electrochemical reactions and respective reduction potentials are known in the art. For example, see the CRC Handbook of Physics and Chemistry, 67th Edition, pages D151-D158 (1987), which is incorporated herein by reference.

The electrotransport device 10 also includes electronic control circuitry (not shown) connected to opposite poles of the power source 24. The power source 24 is preferably a 3 volt lithium button cell battery or a thin film battery. An adhesive layer 28, preferably peripherally, adheres the device 10 to the body surface 100. The device 10 may also include a removable liner (not shown) that protects the adhesive layer 28 until the device 10 is applied to the body surface and engaged into operation.

The donor and counter reservoirs 16,18 may be capable of adsorbing and containing a composition suitable for iontophoretic delivery. For example, the reservoir may be a gauze, pad or sponge constructed from cotton or other natural or synthetic adsorbent fabric or material. Preferably, the reservoirs 16,18 also include a hydrophilic polymer and a water medium. More preferably, the reservoirs 16,18 include a solid polymer matrix composed, in part, of a structurally significant, insoluble hydrophilic polymer.

A matrix containing the agent to be delivered may be crosslinked (such as a silastic matrix) or prefabricated and sorbed with the drug solution (such as with using cellulose, woven fiber, pads or sponges as the matrix). Alternatively, the reservoirs 16,18 may include a gel matrix, such as a hydrophilic polymer swellable or soluble in water. Blends of the mentioned polymers may also be used. The polymers may also be linear or crosslinked. Preferably, the total polymer content in the reservoir is between about 2% and 50% by weight. Suitable hydrophilic polymers include those mentioned herein with respect to the membrane layers.

Alternatively, the reservoirs 16,18 may include a hydrophobic polymer to enhance structural rigidity. Preferably, the hydrophobic polymer is heat fusible to enhance lamination of the reservoirs 16,18 to the insulator 20 or other adjacent components. Exemplary hydrophobic polymers include those mentioned herein with respect to the membrane layers.

The matrices may be a polymeric matrix structure made by blending the drug agent or electrolyte (and other components) with an inert polymer. The donor reservoir 16 contains the drug agent to be delivered and the counter reservoir 18 contains an electrolyte, such as a water soluble biocompatible salt. Preferably, the reservoir composition includes about 25–90% by weight of the matrix. A hydrophobic polymer may also be included to maintain an open pore (or microporous) polymer structure facilitating agent flux.

The reservoirs 16,18 may also contain at least one optional material including dyes, pigments, inert fillers, and/or a rheological agent (such as mineral oil and silica). The counter reservoir 18 may also contain at least one optional component including alkali metal salts (such as NaCl), alkaline earth metal salts (such as chlorides, sulfates, nitrates, carbonates or phosphates thereof), organic salts (such as ascorbates, citrates or acetates), electrolytes containing redox species (such as $Cu^{2+}$, $Fe^{2+}$, $Fe^{3+}$, quinone, hydroquinone, $Ag^{1+}$, and $(IO_3)^{1-}$, and other biocompatible salts and buffers. More preferably, the electrolytic salt is sodium chloride to enhance biocompatibility.

A low porosity membrane 30 is positioned between the donor reservoir 16 and the body surface 100. A high porosity membrane 31 is located between the low porosity membrane 30 and a donor reservoir 16. Pores are distributed substantially uniformly throughout the entire thickness of the membranes 30,31 and extend from surface to surface. The electrotransport device 10 may be used to transfer drug and/or therapeutic agent through the body surface 100.

The surface area of contact where drug is transmitted may range from about 1–200 $cm^2$. More preferably, the area is in the range of about 2–30 $cm^2$. The lower end of the area range may be limited by the strength of available power sources and the desired flux rate, whereas the upper end is limited by the amount of body surface available, by the availability of continuous adhesion given the contours of the body, and by patient comfort.

The electrotransport device 10 also includes a controller (not shown) that is preferably adapted and configured to permit a patient to activate and deactivate the device 10. The controller may also be programmed with an on-demand medication regime or programmed to automatically activate and deactivate periodically to, for example, match the natural or circadian patterns of the body. Preferably, a microprocessor controls the current as a function of time and/or generates current waveforms, such as pulses, sinusoidal, ramp up, ramp down, spikes, etc.

The structural components of the present invention may be melt blended, solvent cast or extruded by methods generally known in the art.

Figure 2:
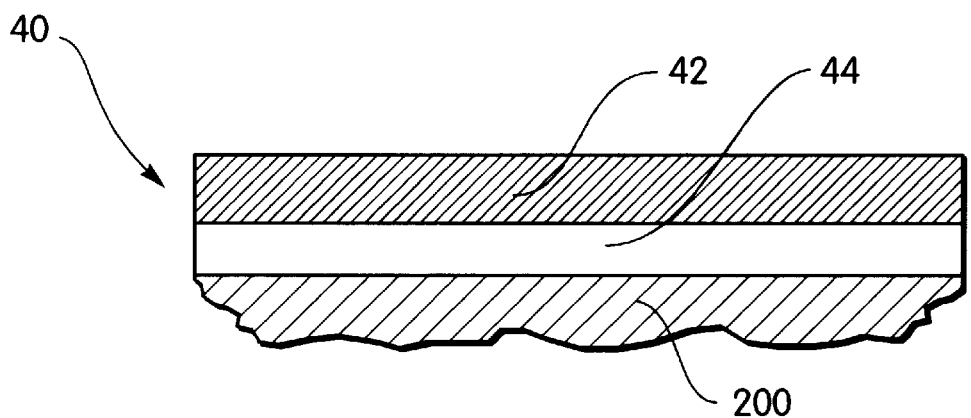
FIG. 2 is a schematic sectional view of an exemplary membrane assembly.

Shown in FIG. 2 is another preferred embodiment of the present invention. The electrotransport device 10 includes a high porosity membrane 44 positioned between a low porosity, rate-controlling membrane 42 and the body surface 200. Preferably, the high porosity membrane has a porosity sufficient to permit a drug delivery rate substantially greater than the therapeutic drug delivery rate. More preferably, the porosity is greater than or equal to about 10%, and even more preferably, greater than or equal to about 20%. Preferably, the low porosity, rate-controlling membrane 42 has a porosity sufficiently low to permit a drug delivery rate substantially equal to a therapeutic drug delivery rate. More preferably, the porosity is less than or equal to about 1%, and even more preferably, less than or equal to about 0.1%. The high porosity layer 44 protects the low porosity layer 42 from oils and particulate contaminates on the body surface 200. Layer 44 also protects the layer 42 from ion-transmitting adhesive when the assembly 40 is affixed to the body surface 200.

Figure 3:
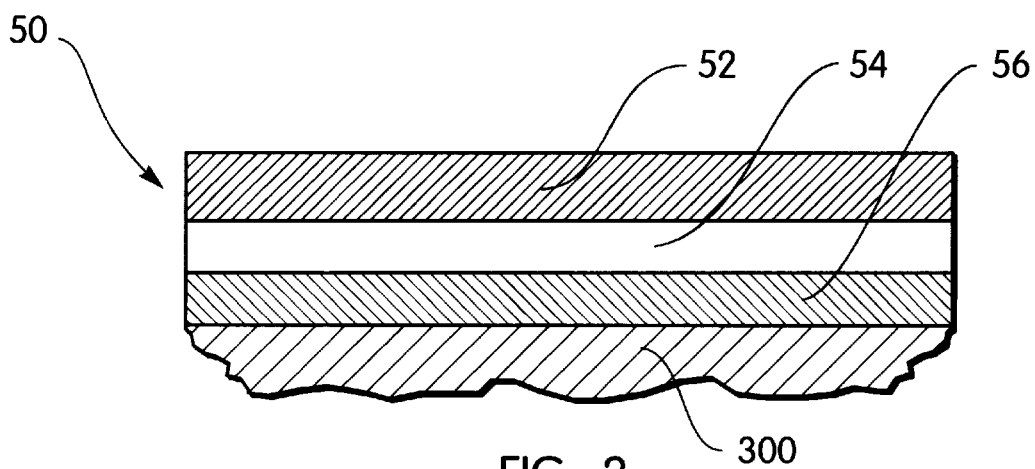
FIG. 3 is a schematic sectional view of another exemplary membrane assembly.

Shown in FIG. 3 is another preferred embodiment of the invention including two high porosity layers 52,56. Membrane 52 is located between the low porosity membrane 54 and the donor or counter reservoir 16,18. The other high porosity membrane 56 is located between the low porosity membrane 54 and the body surface 300. Preferably, the high porosity layer 56 has a porosity greater than or equal to about 10%, and more preferably, greater than or equal to about 20%. The membrane 56 protects the low porosity membrane 54 from occluding or being otherwise damaged. Such damage may be caused by oils, particulates or other contaminates transferred from the body surface.

The layer 56 also protects the membrane 54 from ion-transmitting adhesive that may be coated onto the layer 56 when the assembly 50 is affixed to the body surface 300. As a result, the risk of clogged pores, occlusions and other damage affecting delivery rate are significantly reduced or eliminated. The high porosity membrane 52 protects the low porosity membrane 54 from components and/or contaminates in the donor and/or counter reservoirs 16,18.

Figure 4:
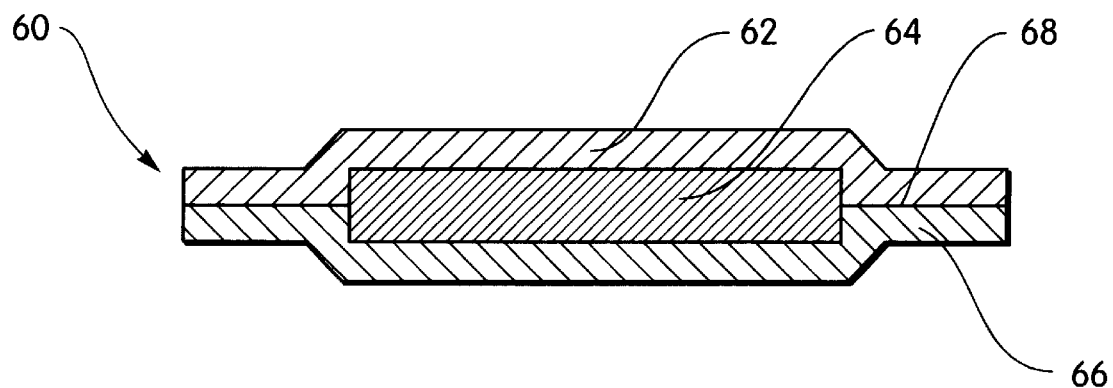
FIG. 4 is a schematic sectional view of an exemplary membrane assembly laminated and sealed with heat and/or pressure; and, FIG. 5 is a schematic sectional view of an exemplary membrane assembly sealed with self-adhering membranes or adhesively sealed.

Shown in FIG. 4 is another preferred embodiment of the invention. The rate-controlling membrane assembly 60 is preferably affixed to the device 10 by laminating along its periphery 68. The assembly 60 includes a low porosity layer 64 positioned between two sealed high porosity layers 62,66 that are affixed along their periphery 68 by heat and/or pressure fusion. The low porosity layer 64 is thereby secured between the outer layers 62,66.

The high porosity membranes of the present invention have preferred pore sizes, size distributions and spatial distributions. For example, preferably, the pores in the high porosity membrane are sufficiently distributed spatially to avoid any significantly uneven agent/drug delivery. Preferably, pore dimensions in the high porosity layer are sufficiently large to permit a drug delivery rate in excess of a therapeutic drug delivery rate. Preferably, the size distribution of the pores is sufficiently narrow to permit a sufficiently even and therapeutic drug delivery rate.

The rate-controlling, low porosity membrane of the present invention also has preferred pore sizes, size distributions, and spatial distributions. Preferably, the pore size of the pores in the low porosity membrane is sufficiently large to substantially permit a therapeutic drug delivery rate and sufficiently small to prevent any significant passive drug or agent delivery. Preferably, the size distribution of the pores in the low porosity layer is sufficiently narrow to prevent significantly uneven drug flux. Preferably, the spatial distribution of the pores in the low porosity layer is sufficiently even to prevent significantly uneven drug flux.

Preferably, the widest average segment of the pore openings in the low porosity membrane is between about 1 millimeter and the molecular size of the drug or agent being delivered. The shape of the pores are, preferably, substantially cylindrical in shape having an average radii between about 0.01 microns and the molecular size of the drug or agent being delivered, and more preferably, between about 0.01 and 5 microns, and even more preferably, between about 0.01 and 200 microns. Preferably, in the high porosity layer membrane, the average pore radii or the widest average segment of the pore openings is greater than 5 microns.

Preferably, the membrane assembly of the present invention is made by a lithographic process capable of high accuracy and precision in terms of porosity and pore distribution, uniformity, size, shape and dimension. One preferred method of making the low porosity membrane is to coat a low porosity substrate with a resistive or energy-sensitive material. A high porosity substrate may be used to form the high porosity membrane. Alternatively, pores may be formed by laser drilling.

The resistive material is cured by exposure to an appropriate energy source. The membrane is removed from the substrate by applying a solvent to uncured resistive material shielded from the energy source. The solvent treatment step is also referred to as chemical etching. A preformed mask may be used to shield a preselected portion of the resistive material.

Exemplary lithographic methods include electron beam lithography, xray lithography, and ion-beam lithography. More preferably, photolithography is used to make the low and high porosity membrane layers of the present invention. Other lithographic processes usable in the present invention include those disclosed in "Encyclopedia of Polymer Science and Engineering," Kirk Othmer's, vol. 11 (1988), which is incorporated, in relevant part, herein by reference.

Preferably, the membrane layers of the present invention is made from an energy-sensitive or resistive material. For example, when a lithographic method is employed, positive and negative image resist materials are preferably used. Such material are disclosed in the "Encyclopedia of Polymer Science and Engineering," vol. 9, pages 97–139 (1987), which is incorporated herein by reference.

Exemplary materials include hydrophilic and hydrophobic polymers. Exemplary hydrophilic polymer include ,copolyesters (such as HYDREL™ from DuPont De Nemours & Co., Wilmington, Del.), polyvinylpyrrolidones, polyvinyl alcohols, polyethylene oxides (such as POLYOX™ from Union Carbide Corp.), CARBOPOL™ from BF Goodrich of Akron, Ohio, blends of polyethylene oxides or polyethylene glycols with polyacrylic acid (such as POLYOX™ blended with CARBOPOL™), polyacrylamides, KLUCEL™, crosslinked dextran (such as SEPHADEX from Pharmacia Fine Chemicals, AB of Uppsala, Sweden), starch grafted poly(sodium acrylate-co-acrylamides (such as WATER LOCK™ from Grain Processing Corp. of Muscatine, Iowa), cellulose derivatives (such as hydroxyethyl celluloses, hydroxypropylmethyl celluloses, low-substituted hydroxypropyl celluloses, and crosslinked sodium carboxymethyl celluloses such as Ac-Di-Sol from FMC Corp. of Philadelphia, Pa), hydrogels (such as polyhydroxylethyl methacrylates available from National Patent Development Corp.), natural gums, chitosans, pectins, starches, guar gums, locust bean gums, blends and combinations thereof, and equivalent materials thereof. Other suitable materials are disclosed in "Handbook of Common Polymers," J. R. Scott & W. J. Roff, (CRC Press, 1971), which is incorporated, in relevant part, herein by reference.

Exemplary hydrophobic polymers for use in making the high and/or low porosity membranes of the present invention include polycarbonates, polyisobutylenes, polyethylenes, polypropylenes, polyisoprenes, polyalkenes, rubbers, KRATON™, polyvinylacetates, ethylene vinyl acetate copolymers, polyamides, nylons, polyurethanes, polyvinylchlorides; acrylic or methacrylic acid esters of an alcohol such as n-butanol, 1-methyl pentanol, 2-methyl pentanol, 3-methyl pentanol, 2-ethyl butanol, iso-octanol, n-decanol, and combinations thereof; such acrylic or methacrylic acid esters of an alcohol copolymerized with one or more ethylenically unsaturated monomers such as acrylic acid, methacrylic acid, acrylamides, methacrylamides, n-alkoxymethyl acrylamides, n-alkoxymethyl methacrylamides, n-tert-butylacrylamides, itaconic acid, n-branched alkyl maleamic acids having 10–24 carbons in the alkyl group, glycol diacrylates, and mixtures and combinations thereof. It is also preferred that the hydrophobic or hydrophilic polymer used to make the low and/or high porosity membrane be heat fusible.

In addition to such materials, the rate-controlling, low porosity membrane is preferably made from a polycarbonate or nylon resin. Preferably, the low porosity membrane made from polycarbonate has a pore size of about 0.01 to 14 microns and a pore density of about $6 \times 10^8$ to $1 \times 10^5$ pores/$cm^2$. Preferably, the low porosity membrane made from nylon has a pore size of about 0.22 to 5.0 microns and a pore density of about $1 \times 10^3$ to $1 \times 10^6$ pores/$cm^2$, and more preferably about about $1 \times 10^3$ to $1 \times 10^4$ pores/$cm^2$.

An exemplary embodiment includes a three layer membrane assembly including a low porosity membrane made from nylon located between two high porosity membranes made from polycarbonate. The low porosity membrane has a pore size of about 1.0 micron, and the high porosity layers have a pore size of about 5.0 microns. The low and high porosity membranes preferably have substantially the same pore density, pore size distribution, and pore spatial distribution. The periphery of the polycarbonate membranes may be sealed with an adhesive, or more preferably, by applying heat and pressure laminating the outer layers.

For example, as is known in the art, the low porosity membrane may be made by gamma irridiating a polycarbonate membrane. The irridiated membrane is then chemically etched with, for example, sodium hydroxide, as is known in the art.

The electrotransport device of the present invention is used to deliver a therapeutic agent and/or drug to the body surface of a patient, such as skin, mucosa or nails. For a given set of operating parameters (e.g. porosity, electrical current, contact area, molecular size, flux rate, etc.), the drug or agent is present in the reservoir in a concentration sufficient to deliver a therapeutic amount or concentration through the skin.

As used herein, "agent" is to be given its broadest reasonable interpretation in the art and includes drugs that produce desirable and generally beneficial effects. For example, "agent" includes therapeutic compounds and molecules from all therapeutic categories including, but not limited to, anti-infectives (such as antibiotics and antivirals), analgesics (such as fentanyl, sufentanil, buprenorphine, and analgesic combinations), anesthetics, antiarthritics, antiasthmatics (such as terbutaline), anticonvulsants, antidepressants, antidiabetics, antidiarrheals, antihistamines, anti-inflammatories, antimigranes, antimotion sickness preparations (such as scopolamine and ondansetron), antineoplastics, antiparkinsonisms, antipruritics, antipsychotics, antipyretics, antispasmodics (including gastrointestinal and urinary), anticholinergics, sympathomimetrics, xanthine and derivatives thereof, cardiovascular preparations (including calcium channel blockers such as nifedipine, beta-agonists (such as dobutamine and ritodrine), beta blockers, antiarrythmics, antihypertensives (such as atenolol), ACE inhibitors (such as lisinopril), diuretics, vasodilators (including general, coronary, peripheral and cerebral), central nervous system stimulants, cough and cold preparations, decongestants, diagnostics, hormones (such as parathyroid hormones), hypnotics, immunosuppressives, muscle relaxants, parasympatholytics, parasympathomimetrics, prostaglandins, proteins, peptides, psychostimulants, sedatives and tranquilizers.

More preferably, the electrotransport device of the present invention delivers drugs and/or agents including baclofen, beclomethasone, betamethasone, buspirone, cromolyn sodium, diltiazem, doxazosin, droperidol, encainide, fentanyl, hydrocortisone, indomethacin, ketoprofen, lidocaine, methotrexate, metoclopramide, miconazole, midazolam, nicardipine, piroxicam, prazosin, scopolamine, sufentanil, terbutaline, testosterone, tetracaine and verapamil.

In an exemplary embodiment, the electrotransport device of the present invention also delivers peptides, polypeptides, proteins and other macromolecules. Such molecules are known in the art to be difficult to deliver transdermally or transmucosally due to their size. For example, such molecules may have molecular weights in the range of 300–40,000 daltons and include, but not limited to, LHRH and analogs thereof (such as buserelin, gosserelin, gonadorelin, naphrelin and leuprolide), GHRH, GHRF, insulin, insulinotropin, heparin, calcitonin, octreotide, endorphin, TRH, NT-36 or N[[(s)-4-oxo-2-azetidinyl]carbonyl]L-histidyl-L-prolinamide], liprecin, pituitary hormones (such as HGH, HMG, HCG, desmopressin acetate), follicile luteoids, α-ANF, growth factor releasing factor (GFRF), β-MSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hirulog, hyaluronidase, interferon, interleukin-2, menotropins (such as urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1 antitrypsin (recombinant), and TGF-beta.

The electrotransport device of the present invention is particularly advantageous for delivering high potency drugs and drugs having dangerous side effects, such as narcotics. For example, the present membrane assembly can prevent or significantly reduce the risk of overdosing (inadvertent or intentional) by eliminating or substantially reducing passive flux of the drug or agent.

Figure 5:
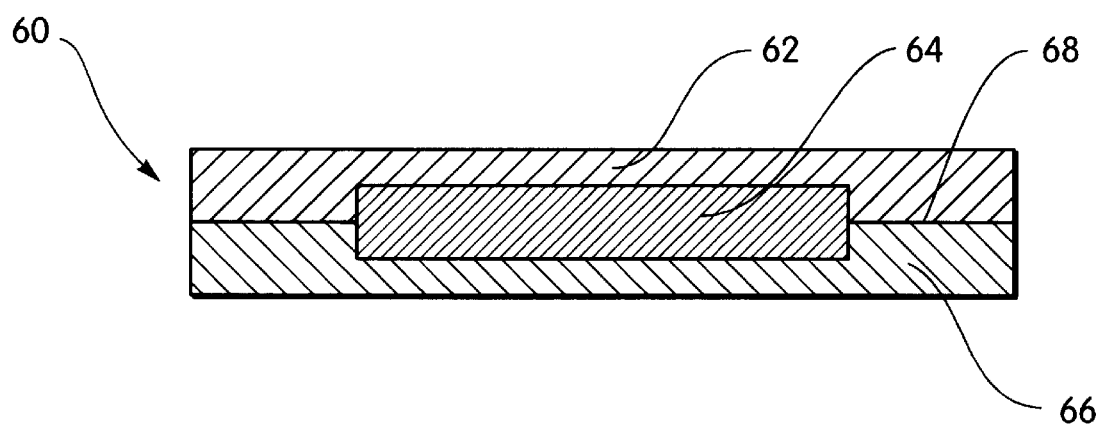

As shown in FIG. 5, the membrane assembly 60 may be sealed with an adhesive along peripheral interface 68. An adhesive is particularly preferred when the membranes do not heat/pressure seal well or when the membranes do not self-adhere. Preferred adhesives include STAYBELITE™ ester Nos. 5 and 10; or, REGAL-REZ™ or PICCOTAC™ available from Hercules Corporation of New Jersey.

As shown in FIG. 5, the membrane assembly 60 may also be sealed by employing upper and lower high porosity membranes 62,66 that are self-adhering along the peripheral surface interface 68. When sealed, the low porosity membrane 64 is contained within the high porosity membranes 62,66. Preferred self-adhering materials include polystyrenebutadiene, poly(styrene-isoprene-styrene) block copolymers, polyisobutylene copolymers, and the polymers disclosed in U.S. Pat. Nos. 4,391,278; 4,474,570; and 4,702,732, which are incorporated herein by reference.

Having generally described the invention and described in detail the preferred embodiments thereof, it will be readily apparent that the invention may be modified or equivalents substituted thereof without departing from the scope of the invention.

Wherein, what is claimed is:

1. An electrotransport device for delivering a therapeutic agent through a body surface comprising:
   a controller,
   a power source,
   a counter electrode assembly, and
   at least one donor electrode assembly including an electrode, a donor reservoir containing the agent, and a membrane assembly located on the body surface distal side of the donor electrode assembly, said membrane assembly comprising:
      a first membrane having a first average pore size, porosity, pore size distribution, and spatial pore distribution affixed to
      a second membrane having a second average pore size, porosity, pore size distribution, and spatial pore distribution,
         wherein the first porosity is less than the second porosity.

2. The electrotransport device of claim 1 wherein said second membrane is located between said reservoir and said first membrane.

3. The electrotransport device of claim 1 wherein said first membrane is located between said reservoir and said second membrane.

4. The electrotransport device of claim 1 wherein said membrane assembly further includes a third membrane having a third average pore size, porosity, pore size distribution, and spatial pore distribution and said first membrane is affixed between said second membrane and said third membrane, wherein said third porosity is greater than said first porosity.

5. The electrotransport device of claims 1, 2, 3, or 4, wherein said first membrane is sufficiently porous to permit at least a therapeutically effective flux of said agent.

6. The electrotransport device of claims 1, 2, or 3 wherein said first porosity is less than or equal to about 1% and said second porosity is greater than or equal to about 10%.

7. The electrotransport device of claim 4 wherein said first porosity is less than or equal to about 1% and said second and third porosities are greater than or equal to about 10%.

8. The electrotransport device of claims 1, 2, or 3 wherein said first porosity is less than or equal to about 0.1% and said second porosity is greater than or equal to about 20%.

9. The electrotransport device of claim 4 wherein said first porosity is less than or equal to about 0.1% and said second and third porosities are greater than or equal to about 20%.

10. The device of claims 1, 2, 3, or 4 having a body surface contact area of about 2 to about 30 cm$^2$, wherein said first average pore size is in the range of about 0.22 to about 5.0 microns and the said first pore density is in the range of about $1 \times 10^3$ to about $1 \times 10^6$ pores/cm$^2$.

11. The device of claim 10 wherein said first pore density is in the range of about $1 \times 10^3$ to about $1 \times 10^4$ pores/cm$^2$.

12. The device of claims 1, 2, or 3 wherein the first average pore size and the second average pore size are in the range of about 1 mm to about the molecular size of the agent.

13. The device of claim 4 wherein the first average pore size, the second average pore size and the third average pore size are in the range of about 1 mm to about the molecular size of the agent.

14. The device of claims 1, 2, 3, or 4 wherein the first average pore size is in the range of about 0.01 microns to about 200 microns.

15. The device of claims 1, 2, or 3 wherein the first average pore size is about 1 micron and the second average pore size is about 5.0 microns.

16. The device of claim 4 wherein the first average pore size is about 1 micron and the second average pore size and the third average pore size are about 5.0 microns.

* * * * *